United States Patent [19]

Wade et al.

[11] 3,959,286

[45] May 25, 1976

[54] N-{1-[(1,3-DIHYDRO-1,3-DIOXO-2H-BENZ[DE]-ISOQUINOLIN-2-YL)ALKYL]-4--PIPERIDINYL}-N-PHENYLALKYLAMIDES

[75] Inventors: Peter C. Wade, Pennington, N.J.; Berthold Richard Vogt, Yardley, Pa.

[73] Assignee: E. R. Squibb & Sons, Inc., Princeton, N.J.

[22] Filed: Jan. 6, 1975

[21] Appl. No.: 538,977

[52] U.S. Cl. .................. 260/281 NH; 260/281 S; 424/258
[51] Int. Cl.² ........................................ C07D 401/06
[58] Field of Search..... 260/281 NH, 281 S, 281 NS

[56] References Cited
UNITED STATES PATENTS 3,247,208  4/1966  Schenker ........................... 260/281
3,625,947  12/1971 Noguchi ............................. 260/281

Primary Examiner—Raymond V. Rush
Assistant Examiner—Mark L. Berch
Attorney, Agent, or Firm—Lawrence S. Levinson; Merle J. Smith; Stephen B. Davis

[57] ABSTRACT

Compounds of the following formula and their acid addition salts

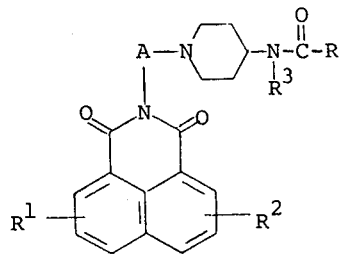

wherein $R^1$ and $R^2$ are independently selected from hydrogen, halogen, lower alkyl, lower alkoxy, lower alkylthio, nitro, cyano, amino and trifluoromethyl; A is a straight or branched chain alkylene of 1 to 8 carbons; $R^3$ is phenyl or substituted phenyl; and R is lower alkyl or cycloalkyl of 3 to 7 carbons are disclosed. These compounds exhibit antidepressant activity. In addition these compounds are useful as antiinflammatory agents.

9 Claims, No Drawings

N-[1-[(1,3-DIHYDRO-1,3-DIOXO-2H-BENZ[DE]-ISOQUINOLIN-2-YL)ALKYL]-4-PIPERIDINYL]-N-PHENYLALKYLAMIDES

BACKGROUND OF THE INVENTION

Various naphthalimide compounds have been developed for use as dyes and optical brightening agents. Kimura et al., for example, at Chem. Abst., Vol. 62, 11950c, disclose N-[2-piperidinoethyl]-4-methoxy-1,8-naphthalimide (i.e. 6-methoxy-2-[2-(1-piperidinyl)ethyl]-1H-benz[de]isoquinoline-1,3(2H)-dione under the current Chem. Abst. nomenclature) as an optical brightening agent. Noguchi et al. in U.S. Pat. No. 3,625,947 disclose 2-[2-(2 or 4-pyridyl)ethyl]-1H-benz[de]isoquinoline-1,3(2H)-diones as fluorescent whitening agents.

Schenker et al. in U.S. Pat. No. 3,247,208 disclose that 1H-benz[de]isoquinoline-1,3(2H)-diones having a (1-substituted-4-piperidinyl) group in the 2-position possess anesthetic properties. Carron et al. in French Pat. No. 2,167,355 disclose that (4-phenyl)piperidine-2,6-diones having an alkylheteroalkyl substituent at the 1-position possess antidepressant activity. Imides having a nitroimidazolyethyl group as an N-substituent and possessing anti-bacterial and antiprotozoal activity are disclosed in U.S. Pat. Nos. 3,642,836 and 3,770,763 to Cusic et al. Certain imido dicarboxylic acid imides possessing various pharmacological properties are disclosed in U.S. Pat. No. 3,560,495 to Frankus et al.

Janssen in U.S. Pat. Nos. 3,164,600 and 3,161,637 discloses N-aralkyl-4-piperidyl-N-arylalkanamides possessing analgesic activity and N-aroylpropyl-4-piperidyl-N-arylalkanamides possessing neuroleptic activity.

SUMMARY OF THE INVENTION

This invention relates to new N-[1-[(1,3-dihydro-1,3-dioxo-2H-benz[de]isoquinolin-2-yl)alkyl]-4-piperidinyl]-N-phenylalkylamides and their acid addition salts of the formula (I)

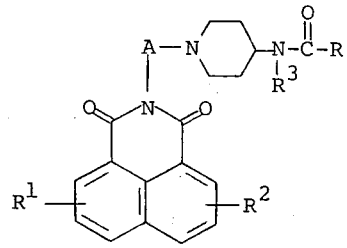

The symbols have the following meaning in formula I and throughout this specification.

$R^1$ and $R^2$ are each independently selected from hydrogen, halogen (preferably Br, Cl, or F), $CF_3$, lower alkyl, lower alkoxy, lower alkylthio, nitro, amino and cyano.

A is straight or branched chain alkylene of 1 to 8 carbons.

R is lower alkyl of 1 to 4 carbons or cycloalkyl of 3 to 7 carbons.

$R^3$ is phenyl or substituted phenyl.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The lower alkylthio group include such lower alkyl groups attached to a sulfur, e.g., methylthio, ethylthio, etc.

Straight or branched chain alkylene of 1 to 8 carbons is intended to include groups such as —$(CH_2)_n$— wherein n is 1 to 8,

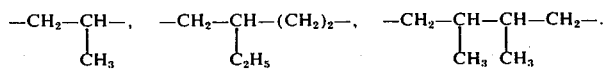

etc.

The substituted phenyl group includes one or more substituents such as lower alkyl, lower alkoxy, lower alkylthio, halogen (preferably F, Cl, or Br), $CF_3$, amino, nitro and the like. Examples of the type of groups contemplated are o-, m- or p-chlorophenyl, o-, m-, or p-tolyl, 2,5-dibromophenyl, 3,5-dimethylphenyl, o-, m-, or p-methoxyphenyl, etc.

Preferred embodiments of this invention are as follows:

At least one of $R^1$ and $R^2$ is hydrogen and the other is hydrogen, Cl, F, Br, $CH_3$ or $OCH_3$.

$R^3$ is phenyl or substituted phenyl wherein the substituent is Cl, F, Br, $CH_3$ or $OCH_3$.

A is straight or branched chain alkylene of 1 to 6 carbons.

R is lower alkyl.

The most preferred compounds are:

$R^1$ and $R^2$ are both hydrogen.

$R^3$ is phenyl.

A is —$(CH_2)_n$— wherein n is an integer from 2 to 6.

The new compounds of this invention are prepared by the following reactions where A is straight or branched chain alkylene of 2 to 8 carbons.

The substituted naphthalic anhydride of formula II (II)

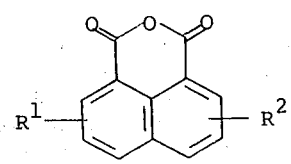

is reacted with an alkanolamine of formula III

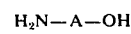 (III)

to yield the alcohol of formula IV (IV)

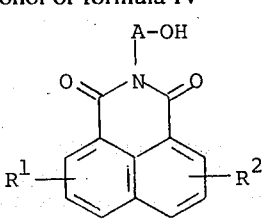

The alcohol of formula IV is converted to the intermediate of formula V (V) 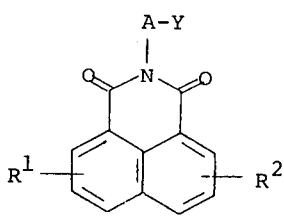

(VII)

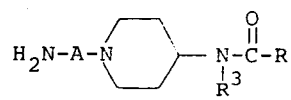

The following schematic summarizes the reactions described above, where A is straight or branched chain alkylene of 2 to 8 carbons.

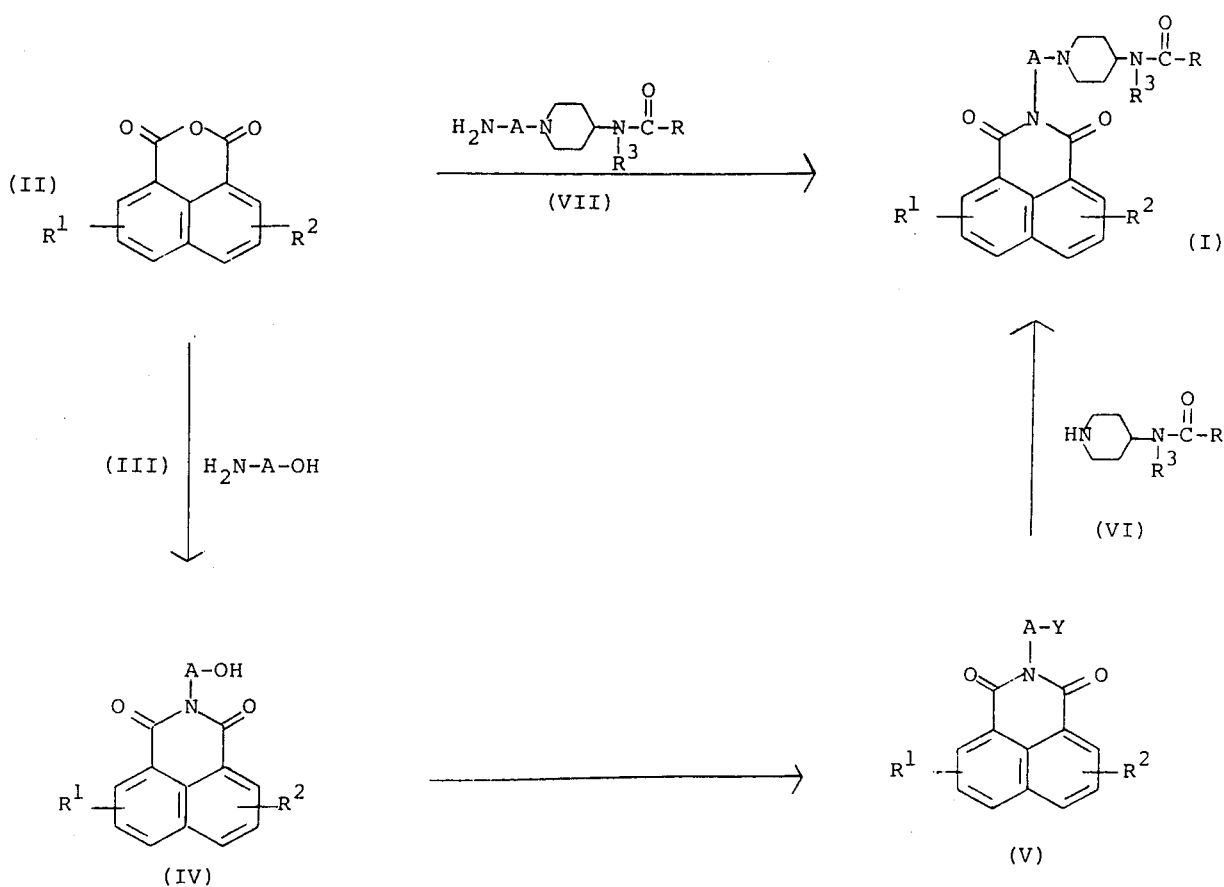

where Y is a leaving group such as tosylate, methane sulfonate or halogen by treating the alcohol with p-toluenesulfonyl chloride, methane sulfonyl chloride, thionyl chloride, thionyl bromide or hydrogen iodide.

The intermediate of formula V is then converted to the final products of formula I by reactions with compounds of the formula (VI)

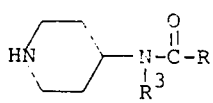

The substituted naphthalic anhydride of formula II can be converted directly to the final products of formula I by reacting the anhydride with compounds of formula VII.

Also, the intermediate of formula V can be prepared by combining a substituted naphthalimide of formula VIII (VIII) 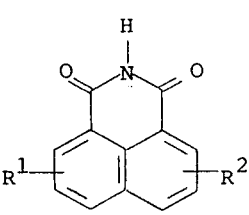

in an organic solvent with a polar organic solvent solution of a base, as, for example, an alcohol solution of potassium hydroxide, followed by the addition of a solution of the compound of formula IX, $$Y'-A-Y \qquad (IX)$$

wherein Y' and Y are the same or different and are leaving groups selected from tosylate, methane sulfonate, or halogen and A is a straight or branched chain alkylene of 2 to 8 carbons.

Alternatively, the compounds of formula I wherein A is straight or branched alkylene of 2 to 8 carbons can be prepared by combining the anion of the substituted naphthalimide of formula VIII, described above, with a solution of the compound of formula X, (X) 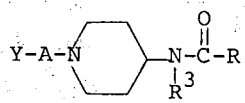

wherein Y is a leaving group as previously defined.

Compounds of formula I where A is —CH$_2$— are prepared by reacting the substituted naphthalimide of formula VIII suspended in a polar organic solvent, such as dimethylformamide (DMF), with compounds of the formula VI and a source of formaldehyde such as aqueous formaldehyde or paraformaldehyde.

The various starting materials such as the substituted anhydrides of formula II, the alcohols of formula IV, the substituted naphthalimides of formula VIII, and the piperidines of formula VI and VII are known in the art or are readily obtainable by known procedures. Further process details are also provided in the illustrative examples.

The compounds of formula I wherein either or both of R$^1$ and R$^2$ is amino, or R$^3$ is phenyl having an amino substituent, are prepared by reducing the corresponding nitro substituted compound with a reducing agent such as hydrogen over a palladium catalyst or a suitable chemical reducing agent. This is preferably done as the last stage in the reaction procedures described above.

Depending on the reaction conditions and the starting materials used, the new compounds are obtained in the free form or in the form of their acid addition salts. The salts thereof can be converted into the free compounds in a known manner such as by reaction with a basic agent. Free bases which may be obtained can be converted into pharmaceutically acceptable acid addition salts by reaction with a variety of acids. Acids useful for preparing these acid-addition salts include, inter alia, inorganic acids, such as the hydrohalic acids (e.g. hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, nicotinic, methanesulfonic or cyclohexanesulfamic.

The new compounds of the present invention including the acid addition salts are capable of modifying the central nervous system. When administered to mice, cats, rats, dogs, and other mammalian species in amounts ranging from about 0.5 mg. to about 100 mg. per kg. of body weight per day, these compounds in particular exhibit antidepressant activity. A preferred dosage regimen for optimum results would be from about 1 mg. to about 5 mg. per kg. of body weight per day, and such dosage units are employed so that a total of from about 35 mg. to about 3 g. of active ingredient in single or divided doses are administered in a 24 hour period.

The antidepressant activity of the compounds of formula I is demonstrated by their ability to antagonize tetrabenazine-induced ptosis according to the procedure of Vernier et al. ("The Pharmacodynamics of Amitriptyline", *Psychosomatic Medicine*, (1962), pages 683–690) and also by their ability to block the reuptake of monoamines in vitro according to the procedure of Horn et al. (*Molecular Pharmacology*, 7th Ed., (1971), page 66).

The compounds of formula I are also useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg. to about 15 mg. per kg. of body weight per day.

For either of these pharmaceutical purposes a compound or mixture of compounds of formula I or their pharmaceutically acceptable acid addition salts may be administered orally or parenterally in a conventional dosage form such as tablet, capsule, injectable or the like. These may be conventionally formulated in an oral or parenteral dosage form by compounding with a conventional vehicle, excipient, binder, preservative, stabilizer, flavor or the like as called for by accepted phamaceutical practice.

The following examples are illustrative of the invention and represent preferred embodiments. Other modifications may be readily produced by suitable variations of the reactions. All temperatures are on the centigrade scale.

EXAMPLE 1

N-[1-[2-(1,3-Dihydro-1,3-dioxo-2H-benz- [de]isoquinolin-2-yl)ethyl]-4-piperidinyl]-N-phenyl- propanamide, hydrochloride (1:1)

a. 2-(2-Hydroxyethyl)-1H-benz[de]isoquinoline- 1,3(2H)-dione 50 g. (0.252 mole) of naphthalic anhydride and 16 g. (0.262 mole) of ethanolamine are refluxed for 3 hours in 200 ml. of water (the solution is never complete). After cooling to 25° the water is decanted off and the residue recrystallized from 95% ethanol to yield 47.8 g. of 2-(2-hydroxyethyl)-1H-benz[de]isoquinoline- 1,3(2H)-dione; m.p. 172°–173°.

b. 2-(2-Hydroxyethyl)-1H-benz[de]isoquinoline- 1,3(2H)-dione, 4-methylbenzenesulfonate ester 52 g. (0.216 mole) of the 2-(2-hydroxyethyl)-1H- benz[de]isoquinoline-1,3(2H)-dione and 100 g. (0.525 mole) of p-toluenesulfonyl chloride are added to 600 ml. of pyridine previously cooled to 5°. The mixture is shaken briefly then allowed to stand overnignt at 5°. The mixture is then poured into 3000 ml. of ice and water, stirred for 15 minutes and filtered. The insoluble material is stirred with fresh water, filtered off again and dried overnight at 25° (0.1 mm.) yielding 83 g. of 2-(2-hydroxyethyl)-1H-benz[de]isoquinoline-1,3(2H)- dione, 4-methylbenzenesulfonate ester.

c. N-[1-[2-(1,3-Dihydro-1,3-dioxo-2H-benz- [de]isoquinolin-2-yl)ethyl]-4-piperidinyl]-N-phenyl- propanamide, hydrochloride (1:1)

A mixture of 8.1 g. (0.02 mole) of the ester from part (b), 5.0 g. (0.02 mole) of 4-(N-propionylanilino) piperidine and 2.66 g. (0.02 mole) of diisopropylethylamine is refluxed in 400 ml. of toluene for 6 hours. The toluene is evaporated and the residue is dissolved in chloroform, and washed with 10% KOH and water (all aqueous layers are backwashed). The chloroform is evaporated and the residue is crystallized from dioxane/hexane. This material is dissolved in toluene and shaken with 10% HCl until the precipitated oil crystallizes. The crystals are collected from the two phases and washed with water and toluene to yield 6.7 g. of crude salt; m.p. 265°–270°. Recrystallization of the crude salt three times from ethanol followed by drying at 80° under a vacuum yields 4.65 g. of N-[1-[2-(1,3-dihydro-1,3-dioxo-2H-benz[de]isoquinolin-2-yl)ethyl]-4-piperidinyl]-N-phenylpropanamide, hydrochloride (1:1); m.p. 270°–272° (d).

EXAMPLES 2–12

Following the procedure of example 1 but substituting the alkanolamine shown in Col. I for the ethanolamine the following products are obtained wherein A is the radical shown in Col. II.

| Ex. | Col. I | Col. II |
|---|---|---|
| 2 | H₂N—(CH₂)₃—OH | —(CH₂)₃— |
| 3 | H₂N—(CH₂)₄—OH | —(CH₂)₄— |
| 4 | H₂N—(CH₂)₅—OH | —(CH₂)₅— |
| 5 | H₂N—(CH₂)₆—OH | —(CH₂)₆— |
| 6 | H₂N—(CH₂)₇—OH | —(CH₂)₇— |
| 7 | H₂N—(CH₂)₈—OH | —(CH₂)₈— |
| 8 | H₂N—CH₂—CH(CH₃)—CH₂—OH | —CH₂—CH(CH₃)—CH₂— |
| 9 | H₂N—CH(CH₃)—(CH₂)₃—OH | —CH(CH₃)—(CH₂)₃— |
| 10 | H₂N—(CH₂)₃—CH(CH₃)—OH | —(CH₂)₃—CH(CH₃)— |
| 11 | H₂N—CH₂—CH(C₃H₇)—(CH₂)₂—OH | —CH₂—CH(C₃H₇)—(CH₂)₂— |
| 12 | H₂N—CH(CH₃)—CH₂—CH(CH₃)—OH | —CH(CH₃)—CH₂—CH(CH₃)— |

EXAMPLES 13–28

Following the procedure of example 1, but substituting for the 4-(N-propionylanilino)piperidine, the compounds shown below in Col. I, one obtains the products shown in Col. II.

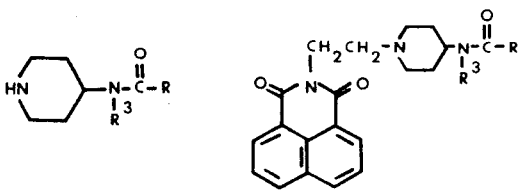

| Ex. | R | R³ |
|---|---|---|
| 13 | —CH₃ | phenyl |
| 14 | n-C₃H₇ | 2-methylphenyl |
| 15 | i-C₃H₇ | 4-ethylphenyl |
| 16 | n-C₄H₉ | 3-methylphenyl |
| 17 | t-C₄H₉ | phenyl |
| 18 | cyclopropyl (—CH—CH₂—CH₂—) | 4-methoxyphenyl |
| 19 | cyclobutyl (—CH—CH₂—CH₂—CH₂—) | 4-trifluoromethylphenyl |
| 20 | cyclopentyl (—CH—(CH₂—CH₂)₂—) | 2-chlorophenyl |
| 21 | cyclohexyl | 4-chlorophenyl |
| 22 | cycloheptyl | 3-bromophenyl |
| 23 | —C₂H₅ | 4-fluorophenyl |
| 24 | —CH₃ | 4-nitrophenyl |

-continued

| Ex. | R | R³ |
|---|---|---|
| 25 | n-C₃H₇ | (phenyl with SC₃H₇) |
| 26 | t-C₄H₉ | (phenyl with NH₂) |
| 27 | —C₂H₅ | (phenyl with Cl, Cl) |
| 28 | —CH₃ | (phenyl with OCH₃, OCH₃) |
| 29 | —C₂H₅ | (phenyl with Cl, Cl) |
| 30 | —C₂H₅ | (phenyl with Cl, CF₃) |

Col. I: piperidine-N-C(O)-R structure
Col. II: benz[de]isoquinoline-CH₂CH₂-piperidine-N-C(O)-R structure Similarly, by employing the compounds of Col. I of examples 13 to 30 in the procedure of examples 2 to 12, other compounds within the scope of the invention are obtained.

EXAMPLE 31

N-[1-[4-(1,3-Dihydro-1,3-dioxo-2H-benz[de]isoquinolin-2-yl)butyl]-4-piperidinyl]-N-phenylpropanamide, hydrochloride a. 2-(4-Bromobutyl)-1H-benz[de]isoquinoline-1,3(2H)-dione 100 g. (0.5 mole) of 1,8-naphthalimide is suspended in 2100 ml. of dimethylformamide and the mixture is heated to 90° to form a complete solution. A solution of 36.3 g. (0.55 mole) of potassium hydroxide (85%) in 100 ml. of methanol is added resulting in the immediate formation of a yellow precipitate. The resulting mixture is stirred for one hour at 90° and cooled to 25°. 245 g. (1.0 mole) of 1,4-dibromobutane is added and the mixture is again heated to 90° and stirred for an additional hour. A precipitate remains in the mixture but is more granular than the initial material. The reaction mixture is cooled and the precipitate filtered off. The solvent is removed under vacuum and the residue is diluted with 500 ml. of hexane immediately precipitating crude 2-(4-bromobutyl)-1H-benz[de]isoquinoline-1,3(2H)-dione. The precipitate is filtered off, washed with fresh hexane and dried for 2 hours at 50° (0.1 mm.) to yield 2-(4-bromobutyl)-1H-benz[de]isoquinoline-1,3(2H)-dione. An analytically pure sample is prepared by dissolving the above product in hot 95% ethanol and recrystallizing by allowing the solution to cool to 25°. The resulting precipitate is dried for 2 hours at 50° (0.1 mm.) to yield pure 2-(4-bromobutyl)-1H-benz[de]isoquinoline-1,3(2H)-dione, m.p. 113°–115°.

b. N-[1-[4-(1,3-Dihydro-1,3-dioxo-2H-benz[de]isoquinolin-2-yl)butyl]-4-piperidinyl]-N-phenylpropanamide, hydrochloride An equimolar mixture of 2-(4-bromobutyl)-1H-benz[de]isoquinoline-1,3(2H)-dione, from part (a), and 4-(N-propionylanilino)piperidine and a molar excess of sodium carbonate are combined in 200 ml. of toluene and refluxed for about 24 hours. The mixture is cooled to room temperature, water is added, and the resulting mixture is shaken and filtered. The organic layer is washed with water, dried, and the solvent removed under vacuum. The residue is dissolved in warm absolute ethanol and treated with 10% excess of ethereal.HCl. The resulting precipitate is filtered off and dried to yield N-[1-[4-(1,3-dihydro-1,3-dioxo-2H-benz[de]isoquinolin-2-yl)butyl]-4-piperidinyl]-N-phenylpropanamide, hydrochloride.

EXAMPLE 32

N-[1-[5-(1,3-Dihydro-1,3-dioxo-2H-benz[de]isoquinolin-2-yl)pentyl]-4-piperidinyl]-N-phenylpropanamide, hydrochloride a. 2-(5-Bromopentyl)-1H-benz[de]isoquinoline-1,3(2H)-dione Following the procedure of part (a) of example 31 but substituting 1,5-dibromopentane for the 1,4-dibromobutane, one obtains 2-(5-bromopentyl)-1H-benz[de]isoquinoline-1,3(2H)-dione; m.p. 113°–115°.

b. N-[1-[5-(1,3-Dihydro-1,3-dioxo-2H-benz[de]isoquinolin-2-yl)-pentyl]-4-piperidinyl]-N-phenylpropanamide, hydrochloride Following the procedure of part (b) of example 31 but substituting 2-(5-bromopentyl)-1H-benz[de]isoquinoline-1,3(2H)-dione for the 2-(4-bromobutyl)-1H-benz[de]isoquinoline-1,3(2H)-dione, one obtains N-[1-[5-(1,3-dihydro-1,3-dioxo-2H-benz[de]isoquinolin-2-yl)pentyl]-4-piperidinyl]-N-phenylpropanamide, hydrochloride.

EXAMPLE 33

N-[1-[6-(1,3-Dihydro-1,3-dioxo-2H-benz[de]isoquinolin-2-yl)hexyl]-4-piperidinyl]-N-phenylpropanamide, hydrochloride a. 2-(6-Bromohexyl)-1H-benz[de]isoquinoline-1,3(2H)-dione Following the procedure of part (a) of example 31 but substituting 1,6-dibromohexane for the 1,4-dibromobutane, one obtains 2-(6-bromohexyl)-1H-benz[de]isoquinoline-1,3(2H)-dione; m.p. 95°–96°.

b. N-[1-[6-(1,3-Dihydro-1,3-dioxo-2H-benz[de]isoquinolin-2-yl)hexyl]-4-piperidinyl]-N-phenylpropanamide Following the procedure of part (b) of example 31 but substituting 2-(6-bromohexyl)-1H-benz[de]isoquinoline-1,3(2H)-dione for the 2-(4-bromobutyl)-1H-benz[de]isoquinoline-1,3-(2H)-dione, one obtains N-[1-[6-(1,3-dihydro-1,3-dioxo-2H-benz[de]isoquinolin-2-yl)hexyl]-4-piperidinyl]-N-phenylpropanamide, hydrochloride.

EXAMPLES 35–61

Following the procedure of example 1 but substituting for the 2-(2-hydroxyethyl)-1H-benz[de]isoquinoline-1,3(2H)-dione, 4-methylbenzenesulfonate ester the ester shown in Col. I one obtains the product shown in Col. II.

| Col. I | Col. II |
|---|---|
| (structure with $(CH_2)_2 O_3SC_6H_4CH_3$ group, $X^1$–$X^6$ substituents) | (structure with $(CH_2)_2$–piperidinyl–N(phenyl)–C(O)–$C_2H_5$ group, $X^1$–$X^6$ substituents) |

| Ex. | $X^1$ | $X^2$ | $X^3$ | $X^4$ | $X^5$ | $X^6$ |
|---|---|---|---|---|---|---|
| 35 | H | H | Br | H | H | H |
| 36 | H | Cl | H | H | H | H |
| 37 | H | Br | H | H | H | H |
| 38 | H | F | H | H | H | H |
| 39 | H | I | H | H | H | H |
| 40 | H | H | Cl | H | H | H |
| 41 | H | Cl | H | H | Cl | H |
| 42 | Br | H | H | H | H | H |
| 43 | H | H | Cl | Cl | H | H |
| 44 | H | H | $CH_3$ | H | H | H |
| 45 | H | H | $C_2H_5$ | H | H | H |
| 46 | H | H | $i$-$C_3H_7$ | H | H | H |
| 47 | H | H | $CH_3$ | $CH_3$ | H | H |
| 48 | H | H | $OCH_3$ | H | H | H |
| 49 | H | H | $OC_2H_5$ | H | H | H |
| 50 | H | H | $OC_3H_7$ | H | H | H |
| 51 | H | H | $OCH_3$ | $OCH_3$ | H | H |
| 52 | H | $NO_2$ | H | H | H | H |
| 53 | H | H | $NO_2$ | H | H | H |
| 54 | H | $CF_3$ | H | H | H | H |
| 55 | H | H | $CF_3$ | H | H | H |
| 56 | H | CN | H | H | H | H |
| 57 | H | H | CN | H | H | H |
| 58 | H | H | $NH_2$ | H | H | H |
| 59 | H | $NH_2$ | H | H | H | H |
| 60 | H | $SC_3H_7$ | H | H | H | H |
| 61 | H | H | $SCH_3$ | H | H | H |

Alternatively, the procedure of examples 31–33 can be employed to prepare the compounds of examples 1–30.

EXAMPLE 34

N-[1-[(1,3-Dihydro-1,3-dioxo-2H-benz[de]isoquinolin-2-yl)methyl]-4-piperidinyl]-N-phenylpropanamide An equimolar mixture of 4-(N-propionylanilino)piperidine, aqueous formaldehyde, and 1,8-naphthalimide is suspended in a small amount of dimethylformamide and the mixture is heated until dissolution is complete. The solution is allowed to stand at room temperature and the resulting precipitate is filtered off and dried to yield N-[1-[(1,3-dihydro-1,3-dioxo-2H-benz[de]isoquinolin-2-yl)methyl]-4-piperidinyl]-N-phenylpropanamide.

Similarly, by employing the various piperidines of examples 13 to 30 in the above procedure, other compounds within the scope of the invention are prepared.

Similarly, by employing the ester of Col. I of examples 35–61 in the procedure of examples 13 to 30, other compounds within the scope of this invention are prepared.

Similarly, by following the procedure of examples 2–12, but employing a substituted 1,8-naphthalic anhydride of formula II wherein the substituents are those listed under the headings $X^1$, $X^2$, $X^3$, $X^4$, $X^5$, and $X^6$ in examples 35–61, other compounds within the scope of the invention are prepared. Also, by following the procedure of example 34 but employing a substituted 1,8-naphthalimide of formula VIII wherein the substituents are those listed under the headings $X^1$, $X^2$, $X^3$, $X^4$, $X^5$, and $X^6$ in examples 35 to 61, other compounds within the scope of this invention are prepared.

What is claimed is:
1. A compound of the formula:

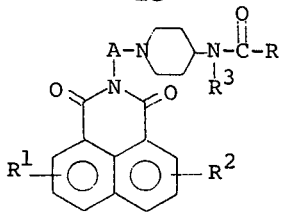

wherein $R^1$ and $R^2$ are each independently selected from the group consisting of hydrogen, halogen, lower alkyl of 1 to 4 carbons, lower alkoxy of 1 to 4 carbons, lower alkylthio of 1 to 4 carbons, nitro, cyano, amino, and trifluoromethyl; A is a straight or branched chain alkylene of 1 to 8 carbons; R is selected from the group consisting of lower alkyl of 1 to 4 carbons and cycloalkyl of 3 to 7 carbons; and $R^3$ is selected from the group consisting of phenyl and substituted phenyl wherein said substituent is lower alkyl of 1 to 4 carbons, lower alkoxy of 1 to 4 carbons, fluorine, bromine, chlorine, di(bromo), di(chloro), di(methyl), di(methoxy), lower alkylthio of 1 to 4 carbons, $CF_3$, nitro or amino; and a pharmaceutically acceptable acid addition salt thereof.

2. The compound of claim 1 wherein at least one of $R^1$ and $R^2$ is hydrogen and the other is selected from the group consisting of hydrogen, Cl, Br, F, methyl and methoxy; and A is a straight or branched chain alkylene of 1 to 6 carbons; R is lower alkyl of 1 to 4 carbons; and $R^3$ is phenyl or substituted phenyl wherein said substituent is Cl, Br, F, methyl or methoxy.

3. The compound of claim 2 wherein $R^1$ and $R^2$ are both hydrogen; $R^3$ is phenyl; and A is a straight chain alkylene of 2 to 6 carbons.

4. The compound of claim 3 wherein A is —$(CH_2)_2$—.

5. The compound of claim 4 having the name N-[1-[2-(1,3-dihydro-1,3-dioxo-2H-benz[de]isoquinolin-2-yl)ethyl]-4-piperidinyl]-N-phenylpropanamide, hydrochloride (1:1).

6. The compound of claim 3 wherein A is —$(CH_2)_3$—.

7. The compound of claim 3 wherein A is —$(CH_2)_4$—.

8. The compound of claim 3 wherein A is —$(CH_2)_5$—.

9. The compound of claim 3 wherein A is —$(CH_2)_6$—.

* * * * *